(12) United States Patent
Anderson et al.

(10) Patent No.: US 8,332,046 B2
(45) Date of Patent: Dec. 11, 2012

(54) NEURAL INTERFACE SYSTEM

(75) Inventors: David J. Anderson, Ann Arbor, MI (US); Rio J. Vetter, Ypsilanti, MI (US); Jamille F. Hetke, Brooklyn, MI (US); Daryl R. Kipke, Dexter, MI (US)

(73) Assignee: NeuroNexus Technologies, Inc., Ann Arbor, MI (US)

( * ) Notice: Subject to any disclaimer, the term of this patent is extended or adjusted under 35 U.S.C. 154(b) by 205 days.

(21) Appl. No.: 12/848,828

(22) Filed: Aug. 2, 2010

(65) Prior Publication Data

US 2011/0093052 A1 Apr. 21, 2011

Related U.S. Application Data

(60) Provisional application No. 61/252,345, filed on Oct. 16, 2009.

(51) Int. Cl.
*A61N 1/05* (2006.01)
(52) U.S. Cl. ........................................ 607/116
(58) Field of Classification Search ........... 607/115–120
See application file for complete search history.

(56) References Cited

U.S. PATENT DOCUMENTS

| | | | |
|---|---|---|---|
| 3,847,687 A | 11/1974 | Davidsohn et al. |
| 3,921,916 A | 11/1975 | Bassous |
| 4,141,365 A | 2/1979 | Fischell et al. |
| 4,166,469 A | 9/1979 | Littleford |
| 4,306,562 A | 12/1981 | Osborne |
| 4,455,192 A | 6/1984 | Tamai |
| 4,461,304 A | 7/1984 | Kuperstein |
| 4,465,482 A | 8/1984 | Tittel |
| 4,762,135 A | 8/1988 | Van Der Puije et al. |
| 4,886,065 A | 12/1989 | Collins, Jr. |
| 4,904,237 A | 2/1990 | Janese |
| 5,108,819 A | 4/1992 | Heller et al. |
| 5,180,376 A | 1/1993 | Fischell |
| 5,207,709 A | 5/1993 | Picha |
| 5,215,088 A | 6/1993 | Normann et al. |

(Continued)

FOREIGN PATENT DOCUMENTS

WO 01/12115 2/2001

(Continued)

OTHER PUBLICATIONS

Application No. PCT/IB06/53700, International Search Report mailed Nov. 21, 2008.

(Continued)

*Primary Examiner* — Brian T Gedeon
(74) *Attorney, Agent, or Firm* — Michael F. Scalise

(57) ABSTRACT

A neural interface system including an electrode array and a carrier that supports the electrode array, in which the electrode array includes a substrate rolled into a three-dimensional shape, a plurality of conductive traces patterned on the substrate and adapted to transmit electrical signals, and a plurality of elliptically shaped, externally facing electrode sites coupled to the plurality of conductive traces that electrically communicate with their surroundings. The plurality of electrodes are arranged in a triangular lattice circumferentially around and axially along the carrier, and the substrate includes an edge that extends axially along the carrier and is constrained between a first axial row portion of the plurality of electrode sites and a second axial row portion of the plurality of electrode sites adjacent to the first axial row portion.

36 Claims, 7 Drawing Sheets

U.S. PATENT DOCUMENTS

| | | | |
|---|---|---|---|
| 5,308,442 | A | 5/1994 | Taub et al. |
| 5,322,064 | A | 6/1994 | Lundquist |
| 5,385,635 | A | 1/1995 | O'Neill |
| 5,390,671 | A | 2/1995 | Lord et al. |
| 5,409,469 | A | 4/1995 | Schaerf |
| 5,496,360 | A | 3/1996 | Hoffmann et al. |
| 5,515,848 | A | 5/1996 | Corbett, III et al. |
| 5,524,338 | A | 6/1996 | Martyniuk et al. |
| 5,573,520 | A | 11/1996 | Schwartz et al. |
| 5,585,827 | A | 12/1996 | Murakami |
| 5,588,597 | A | 12/1996 | Reinecke et al. |
| 5,720,099 | A | 2/1998 | Parker et al. |
| 5,744,958 | A | 4/1998 | Werne |
| 5,800,535 | A | 9/1998 | Howard, III |
| 5,843,150 | A | 12/1998 | Dreessen et al. |
| 5,927,277 | A | 7/1999 | Baudino et al. |
| 5,938,694 | A | 8/1999 | Jaraczewski et al. |
| 5,975,085 | A | 11/1999 | Rise |
| 5,989,445 | A | 11/1999 | Wise et al. |
| 5,992,769 | A | 11/1999 | Wise et al. |
| 6,006,124 | A | 12/1999 | Fischell et al. |
| 6,016,449 | A | 1/2000 | Fischell et al. |
| 6,044,304 | A | 3/2000 | Baudino |
| 6,132,456 | A | 10/2000 | Sommer et al. |
| 6,181,569 | B1 | 1/2001 | Chakravorty |
| 6,205,361 | B1 | 3/2001 | Kuzma et al. |
| 6,228,111 | B1 | 5/2001 | Tormala et al. |
| 6,324,433 | B1 | 11/2001 | Errico |
| 6,325,797 | B1 | 12/2001 | Stewart et al. |
| 6,374,143 | B1 | 4/2002 | Berrang et al. |
| 6,430,443 | B1 | 8/2002 | Karell |
| 6,600,231 | B2 | 7/2003 | Tominaga |
| 6,618,623 | B1 | 9/2003 | Pless et al. |
| 6,829,498 | B2 | 12/2004 | Kipke et al. |
| 6,834,200 | B2 | 12/2004 | Moxon et al. |
| 6,878,643 | B2 | 4/2005 | Krulevitch et al. |
| 7,004,948 | B1 | 2/2006 | Pianca et al. |
| 7,006,859 | B1 | 2/2006 | Osorio et al. |
| 7,010,356 | B2 | 3/2006 | Jog et al. |
| 7,011,680 | B2 | 3/2006 | Alt |
| 7,089,059 | B1 | 8/2006 | Pless |
| 7,181,288 | B1 | 2/2007 | Rezai et al. |
| 7,343,205 | B1 | 3/2008 | Pianca et al. |
| 7,548,775 | B2 | 6/2009 | Kipke et al. |
| 7,871,707 | B2 | 1/2011 | Laude et al. |
| 7,914,842 | B1 | 3/2011 | Greenberg et al. |
| 7,941,202 | B2 | 5/2011 | Hetke et al. |
| 2001/0049499 | A1 | 12/2001 | Lui et al. |
| 2002/0052610 | A1 | 5/2002 | Skakoon et al. |
| 2002/0183817 | A1 | 12/2002 | Van Venrooij et al. |
| 2002/0198446 | A1 | 12/2002 | Hill et al. |
| 2003/0093129 | A1 | 5/2003 | Nicolelis et al. |
| 2003/0100823 | A1 | 5/2003 | Kipke |
| 2003/0114906 | A1 | 6/2003 | Booker et al. |
| 2003/0187461 | A1 | 10/2003 | Chin |
| 2004/0006264 | A1 | 1/2004 | Mojarradi et al. |
| 2004/0102828 | A1 | 5/2004 | Lowry et al. |
| 2004/0106169 | A1 | 6/2004 | Evans |
| 2004/0199235 | A1 | 10/2004 | Younis |
| 2005/0004627 | A1 | 1/2005 | Gibson et al. |
| 2005/0021116 | A1 | 1/2005 | He et al. |
| 2005/0021117 | A1 | 1/2005 | He et al. |
| 2005/0137647 | A1 | 6/2005 | Wallace et al. |
| 2005/0222647 | A1 | 10/2005 | Wahlstrand et al. |
| 2006/0122677 | A1 | 6/2006 | Vardiman |
| 2006/0173263 | A1 | 8/2006 | He et al. |
| 2006/0247749 | A1 | 11/2006 | Colvin |
| 2006/0258951 | A1 | 11/2006 | Bleich et al. |
| 2006/0276866 | A1 | 12/2006 | McCreery |
| 2006/0282014 | A1 | 12/2006 | Kipke et al. |
| 2007/0073130 | A1 | 3/2007 | Finch et al. |
| 2007/0123765 | A1 | 5/2007 | Hetke et al. |
| 2007/0135885 | A1 | 6/2007 | Risi |
| 2008/0132970 | A1 | 6/2008 | Barolat |
| 2008/0208283 | A1 | 8/2008 | Vetter et al. |
| 2008/0255439 | A1 | 10/2008 | Tang et al. |
| 2008/0262584 | A1 | 10/2008 | Bottomley et al. |
| 2009/0099555 | A1 | 4/2009 | Viohl et al. |
| 2009/0102068 | A1 | 4/2009 | Pellinen et al. |
| 2009/0118806 | A1 | 5/2009 | Vetter et al. |
| 2009/0132042 | A1* | 5/2009 | Hetke et al. ............ 623/11.11 |
| 2009/0149934 | A1 | 6/2009 | Ameri et al. |
| 2009/0171421 | A1 | 7/2009 | Atalar et al. |
| 2009/0187196 | A1 | 7/2009 | Vetter et al. |
| 2009/0234426 | A1 | 9/2009 | Pellinen et al. |
| 2009/0240314 | A1 | 9/2009 | Kong et al. |
| 2009/0248118 | A1 | 10/2009 | Bradley et al. |
| 2009/0253977 | A1 | 10/2009 | Kipke et al. |
| 2009/0299167 | A1 | 12/2009 | Seymour |
| 2009/0312770 | A1 | 12/2009 | Kozai et al. |
| 2010/0030298 | A1 | 2/2010 | Martens et al. |
| 2010/0145216 | A1 | 6/2010 | He et al. |
| 2010/0145422 | A1 | 6/2010 | Seymour et al. |
| 2011/0154655 | A1 | 6/2011 | Hetke et al. |

FOREIGN PATENT DOCUMENTS

| | | |
|---|---|---|
| WO | PCT/CA00/00942 | 2/2001 |
| WO | 02/36002 | 5/2002 |
| WO | 0241666 | 5/2002 |
| WO | PCT/EP00/10775 | 5/2002 |
| WO | 02/096482 | 12/2002 |
| WO | PCT/US02/16942 | 12/2002 |
| WO | 2005/039696 | 5/2005 |
| WO | PCT/US2004/035030 | 5/2005 |
| WO | 2006138358 A | 12/2006 |
| WO | 2007042999 A | 4/2007 |
| WO | 2007089738 A | 8/2007 |
| WO | 2008011721 A | 1/2008 |
| WO | 2008038208 A | 4/2008 |
| WO | 2008072125 A | 6/2008 |
| WO | 2008109298 A | 9/2008 |
| WO | 2009052423 A | 4/2009 |
| WO | 2009052425 A | 4/2009 |
| WO | 2010057095 A | 5/2010 |
| WO | 2011/010257 | 1/2011 |
| WO | 2011046665 A | 4/2011 |

OTHER PUBLICATIONS

Application No. PCT/IB10/53250, International Search Report mailed Oct. 4, 2010.

Application No. PCT/US04/35030, International Search Report mailed Feb. 21, 2005.

Application No. PCT/US06/23139, International Search Report mailed Aug. 2, 2007.

Application No. PCT/US07/02465, International Search Report mailed Feb. 13, 2008.

Application No. PCT/US08/55025, International Search Report and Written Opinion mailed Oct. 27, 2008.

Application No. PCT/US08/80364, International Search Report and Written Opinion mailed Dec. 16, 2008.

Application No. PCT/US08/80366, International Search Report and Written Opinion mailed Dec. 10, 2008.

Application No. PCT/US09/64591, International Search Report and Written Opinion mailed Jul. 21, 2010.

Application No. PCT/US10/44167, International Search Report and Written Opinion mailed Sep. 27, 2010.

Lin et al., "Silicon Processed Microneedles," IEEE J. Micro. Electro. Mech. Sys, vol. 8, No. 1 (1999) 78-84 (7 pages).

Seymour, John P., Kipke, Daryl R. "Neural probe design for reduced tissue encapsulation in CNS" 28 (2007) 3594-3607, Apr. 5, 2007.

Seymour, John P., Elkasabi, Yaseen M., Chen, Hsien-Yeh, Lahann, Joerg, Kipke, Daryl R., "The insulation performance of reactive parylene films in implantable electronic devices" Biomaterials 30 (2009) 6158-6167, Aug. 22, 2009.

Kaplan, et al., "A Novel Fabrication Method of Capillary Tubes on Quartz for Chemical Analysis Applications" IEEE Proceedings, Micro Electro Mechanical Systems, Jan. 25-28, 1994.

Lin, et al., "Silicon Processed Microneedles" The 7th International Conference on Solid State Sensors and Acutators; Jun. 7-10, 1993.

U.S. Appl. No. 12/986,081, Hetke.

Seymour, John P., Kipke, Daryl R. "Neural probe design for reduced tissue encapsulation in CNS", 28 (2007) 3594-3607, Apr. 5, 2007.

Seymour, John P., Elkasabi, Yaseen M., Chen, Hsien-Yeh, Lahann, Joerg, Kipke, Daryl R., "The insulation performance of reactive parylene films in implantable electronic devices", Biomaterials 30 (2009) 6158-6167, Aug. 22, 2009.

Kaplan, et al., "A Novel Fabrication Method of Capillary Tubes on Quartz for Chemical Analysis Applications", IEEE Proceedings, Micro Electro Mechanical Systems, Jan. 25-28, 1994.

Lin, et al., "Silicon Processed Microneedles", The 7th International Conference on Solid State Sensors and Acutators; Jun. 7-10, 1993.

\* cited by examiner

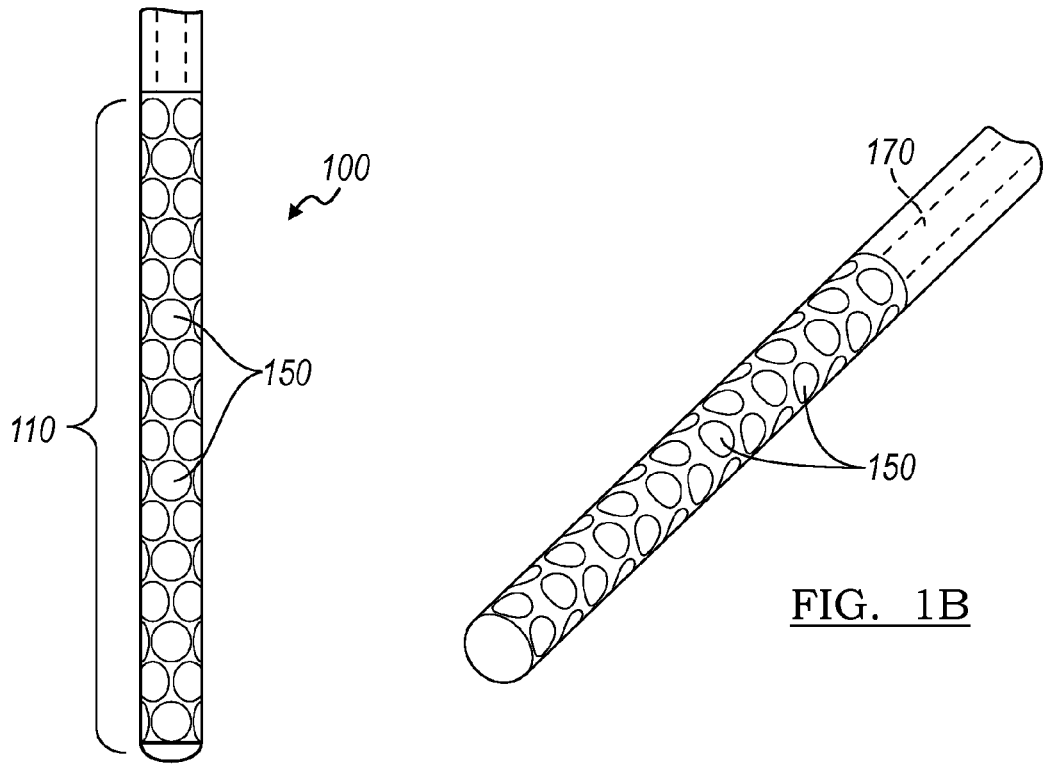
FIG. 1A
FIG. 1B
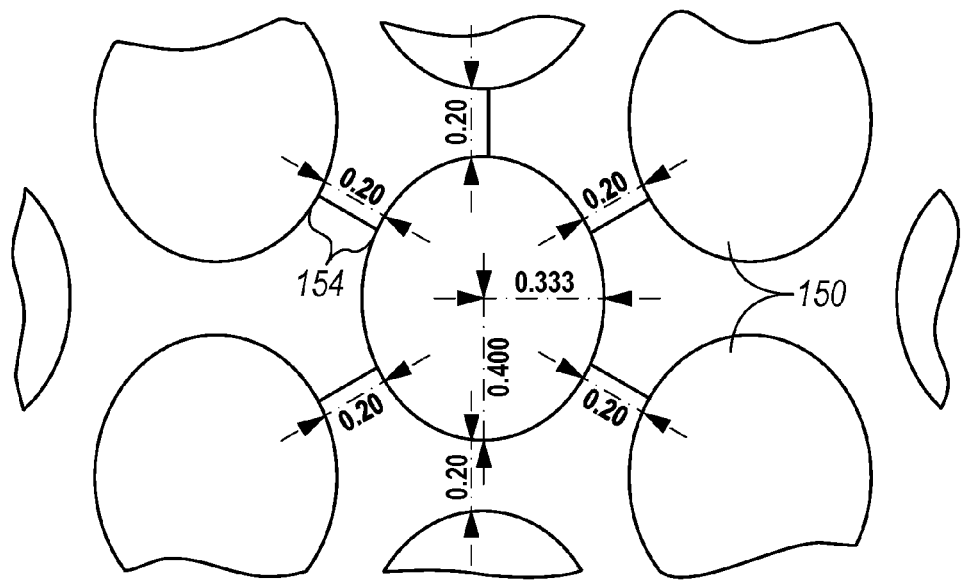
FIG. 2

● ACTIVATED
⊖ NOT ACTIVATED

NEURAL INTERFACE SYSTEM

CROSS-REFERENCE TO RELATED APPLICATIONS

This application claims the benefit of US Provisional Application Ser. No. 61/252,345, filed 16 Oct. 2009, which is incorporated in its entirety by this reference.

TECHNICAL FIELD

This invention relates generally to the neural interface field, and more specifically to an improved neural interface system in the neural interface field.

BACKGROUND

Chronic Deep Brain Stimulation (DBS) devices, or "brain pacemakers", is a treatment of neurological and psychological disorders. Conventional DBS devices provide electrical stimulation through a lead having four relatively large electrodes that are implanted in a targeted region of the brain. While conventional DBS therapy is generally safe and effective for reducing cardinal symptoms of the approved diseases, it often has significant behavioral and cognitive side effects and limits on performance. Additionally, the therapeutic effect is highly a function of electrode position with respect to the targeted volume of tissue, and more specifically, a function of which neuronal structures are influenced by the charge being delivered. With conventional DBS electrodes, there are limitations as to how a charge is delivered, and stimulation fields are limited, as all of the electrode sites involved with stimulation are positioned along a single axis. Thus, there is a need in the neural interface field to create an improved neural interface system that provides fine electrode positioning, selectivity, precise stimulation patterning, and precise lead location. This invention provides such an improved neural interface system.

BRIEF DESCRIPTION OF THE FIGURES

FIGS. 1A and 1B are side and perspective schematic views, respectively, of the neural interface system of a preferred embodiment;

FIG. 2 is a schematic of electrode site spacing on the electrode array of a preferred embodiment;

DESCRIPTION OF THE PREFERRED EMBODIMENTS

Figure 3A:
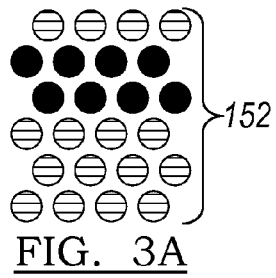
FIGS. 3A, 3B, and 3C are an unwrapped planar view, a perspective view, and a cross-sectional axial view, respectively, of an example activation pattern activating electrode sites circumferentially around the carrier.

The following description of preferred embodiments of the invention is not intended to limit the invention to these preferred embodiments, but rather to enable any person skilled in the art to make and use this invention.

As shown in FIG. 1, the neural interface system 100 of the preferred embodiments includes an electrode array 110 having a substrate 120 rolled into a three-dimensional array shape, a plurality of conductive traces 140 patterned on the substrate 120 and adapted to transmit electrical signals and a plurality of electrode sites 150 coupled to the plurality of conductive traces 140; and a carrier 170 that supports the electrode array. The electrode array is preferably coupled to the carrier 170 such that the electrode sites 150 are arranged in a triangular lattice circumferentially around and axially along the carrier. The substrate 120 preferably includes an edge that extends axially along the carrier and is constrained between a first axial row portion of the carrier and a second axial row portion of the plurality of electrode sites adjacent to the first axial row portion. The electrode sites 150 may include recording electrode sites and/or stimulation electrode sites, and may be individually activated or simultaneously activated as a group to create an activation pattern. The neural interface system 100 preferably provides deep brain stimulation and, more specifically, deep brain stimulation with one or more of the following attributes: fine electrode site positioning, selectivity, tunability, reduced power consumption, increased fault tolerance, and precise activation patterning. The system may alternatively be used in any suitable environment (such as the spinal cord, peripheral nerve, muscle, or any other suitable anatomical location) and for any suitable reason.

1. The Electrode Array

The electrode array 110 of the preferred embodiment functions to interface with tissue, or any suitable substance, that it has been implanted in or coupled to. The electrode array preferably includes a substrate 120, a plurality of conductive traces 140 adapted to transmit electrical signals, and a plurality of electrode sites 150, such that a group of the electrode sites may be simultaneously activated to create an activation pattern. The neural interface system 100 may include a single electrode array with a plurality of electrode sites 150, or may alternatively include a series of electrode arrays, each with a plurality of electrode sites. The electrode array preferably provides the capability of incorporating feedback control through neural recordings for eventual on-demand simulation. The electrode array 110 may further include fluidic channels providing the capability to deliver therapeutic drugs, drugs to inhibit biologic response to the implant, or any other suitable fluid.

The electrode array 110 is preferably has a three dimensional geometry in which the substrate 120 is rolled into a three-dimensional array shape and the conductive traces 140 and the plurality of electrode sites 150 are preferably arranged on and around the three dimensional shape. As further described below, in this variation, the electrode array is preferably manufactured in such a way that none of the electrode sites 150 are obscured. The geometry of the electrode array preferably has a circular or semi-circular cross section, but may alternatively be any suitable geometry with any suitable cross section such as an eccentric ellipse, v-shaped, or a crescent cross section. The three dimensional electrode array is preferably formed by pre-forming a planar electrode array. This is preferably completed by positioning the planar electrode array in a mold and then placing the mold and electrode array in a furnace to be tempered, but may alternatively be completed by any suitable process that alters the physical shape of the planar substrate 120. The three-dimensional electrode array may be wrapped directly around the tissue to be stimulated, such as a peripheral nerve or spinal cord, or in any suitable configuration to interface with tissue, or any other suitable substance, that it has been implanted in or coupled to. In the planar electrode array, the substrate 120 is planar and the conductive traces 140 and electrode sites 150 are arranged on the planar substrate 120. In some embodiments, the planar electrode array may be particularly useful for stimulation of surface tissue such as surface stimulation of the brain or spinal cord. The electrode array may include electrode sites 150 arranged in a staggered layout pattern, a hexagonal layout pattern, a linear rectangular pattern, or any suitable pattern.

Figure 12A:
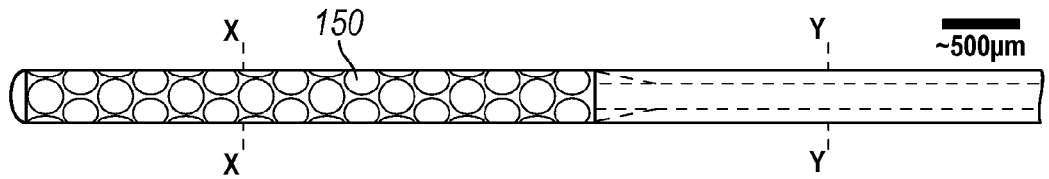
FIG. 12A is a schematic side view of the neural interface system of a preferred embodiment.
Figure 12B:
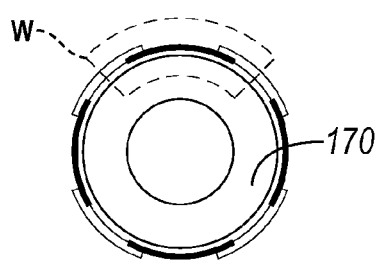
FIG. 12B is a cross-sectional view of the electrode array and carrier taken along the line X-X in FIG. 12A.
Figure 12D:
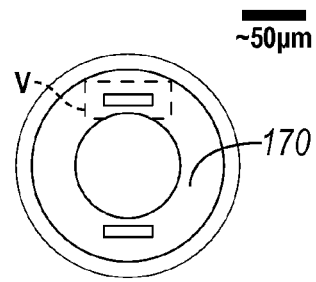
FIG. 12D is a cross-sectional view of the electrode array and carrier taken along the line Y-Y in FIG. 12A.
Figure 12C:
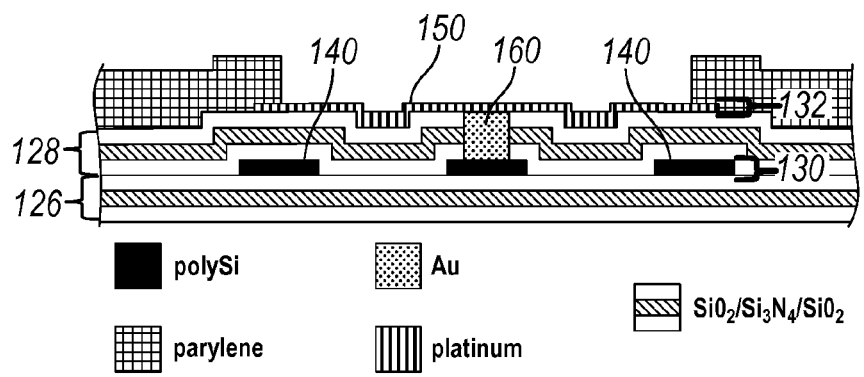
FIG. 12C is a detailed cross-sectional view of the electrode array and carrier taken in panel W in FIG. 12B.
Figure 12E:
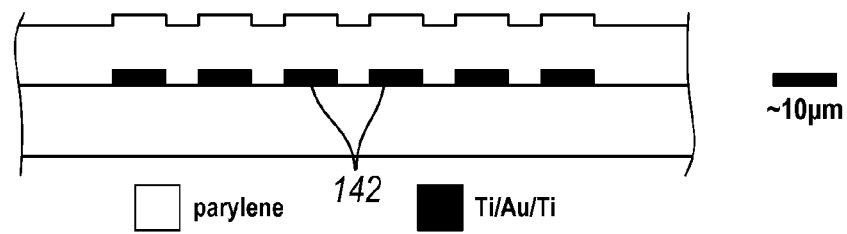
FIG. 12E is a detailed cross-sectional view of the electrode array and carrier taken in panel V in FIG. 12C.
Figure 13:
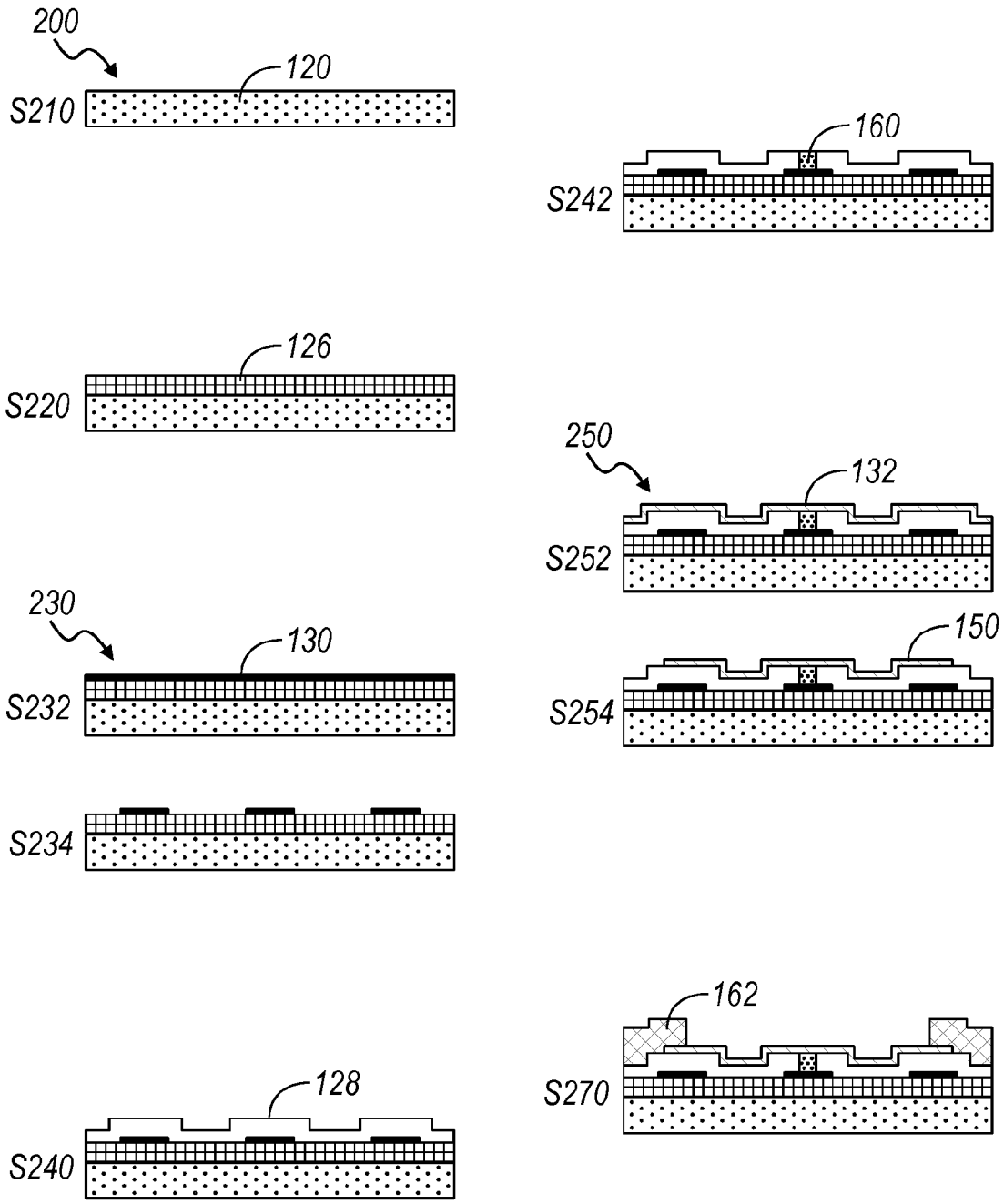
FIG. 13 is an illustration of the steps of making a neural interface system of a preferred embodiment.

The substrate 120 of the electrode array functions to provide a base material onto which layers of material forming the electrode array are deposited. As shown in FIGS. 12 and 13, layers of material deposited on the electrode array preferably include at least one layer of polymer and at least one layer of metal. More preferably, the layers include a first polymer layer 126 and a second polymer layer 128, a first metal layer 130 between the first and second polymer layers used to form the plurality of conductive traces 140, and a second metal layer used to form the plurality of electrode sites 150. The first and second polymer layers preferably include silicon dioxide and silicon nitride, the first metal layer preferably includes polysilicon, and the second metal layer preferably includes platinum. The layers on the substrate 120 preferably further include a third metal layer, such as gold, used to form bond pads 160 that electrically couple the plurality of conductive traces 140 to the plurality of electrode sites 150. The layers on the substrate 120 may further include a third polymer layer 162, such as parylene, that provides an external layer of insulation surrounding the electrode sites 150. However, the substrate 120 may have any suitable number of layers including any suitable materials deposited on the substrate.

Figure 8:
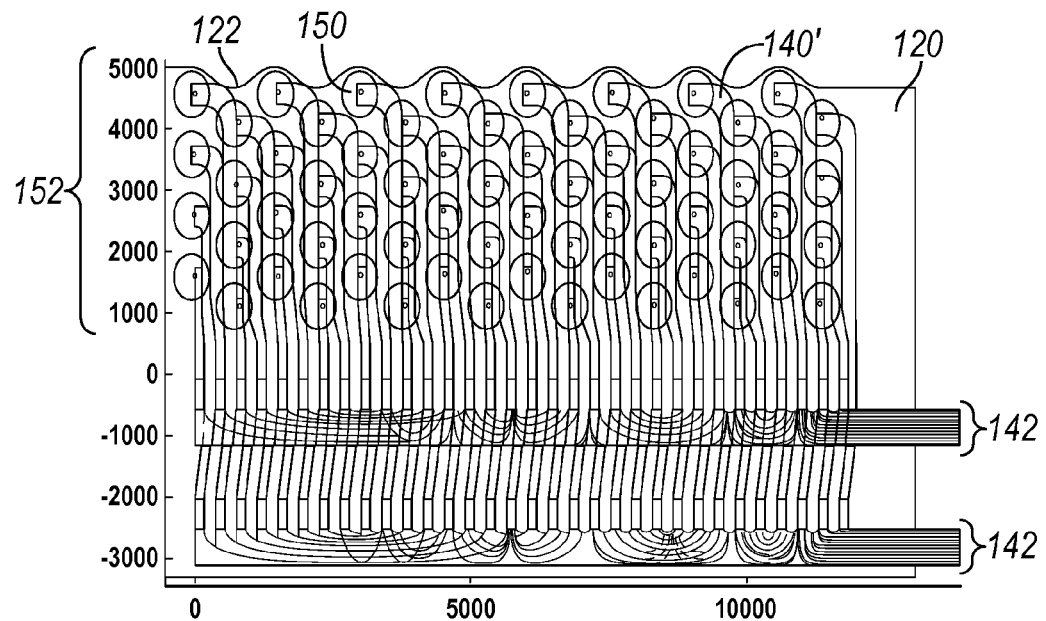
FIG. 8 is a schematic drawing of a variation of the trace layout pattern in the electrode array of a preferred embodiment.
Figure 9:
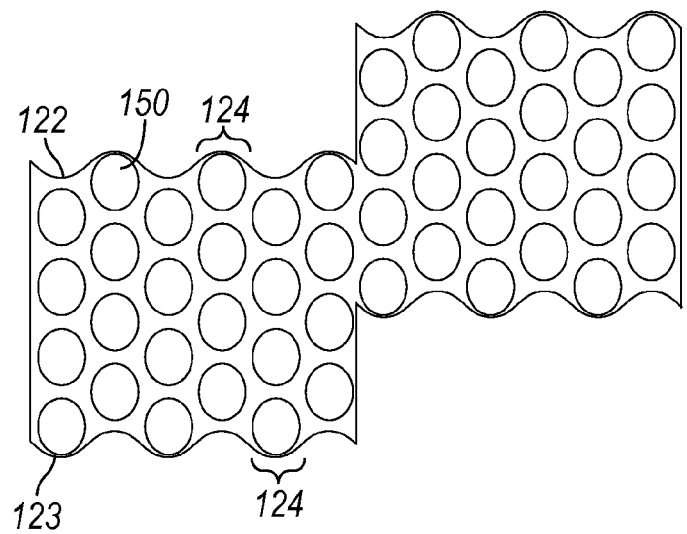
FIG. 9 is a schematic drawing of a variation of the substrate shape in the electrode array of a preferred embodiment.
Figure 10:
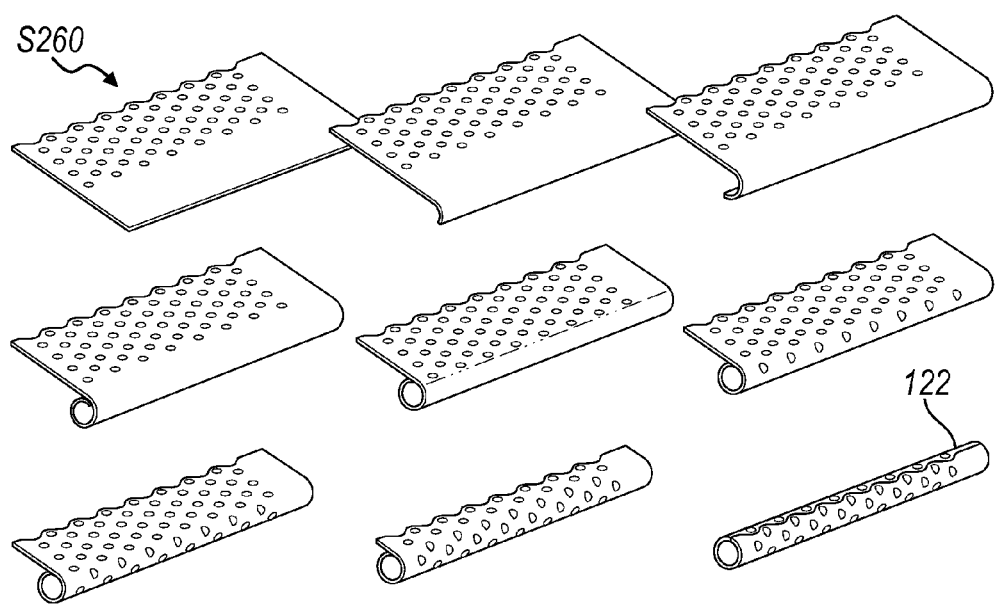
FIG. 10 is a schematic of the wrapping step of forming an electrode array of a preferred embodiment.
Figure 11:
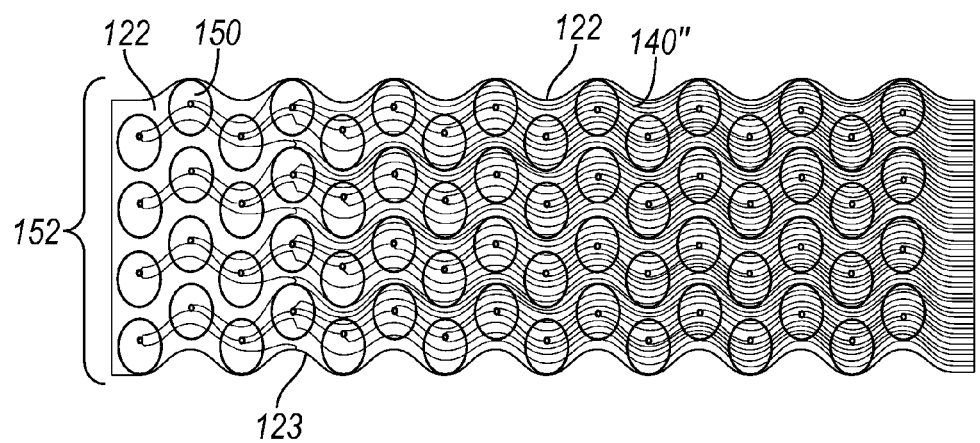
FIG. 11 is a schematic drawing of a second variation of the trace layout pattern in the electrode array of a preferred embodiment.

Since a triangular lattice or other staggered electrode site pattern cannot be parted by a single straight line in an axial direction along the carrier, such a staggered electrode site pattern cannot be laid onto a rectangular substrate without having obscured or covered electrode sites, extra substrate space unpopulated by electrode sites 150, or overlap of substrate when forming a three-dimensional electrode array from a planar electrode array. As shown in FIGS. 8-11, to avoid obscuring electrode sites, in some preferred embodiments, the substrate 120 preferably has at least one axial edge 122 that is constrained between a first axial row portion of the plurality of electrode sites and a second axial row portion of the plurality of electrode sites adjacent to the first axial row portion. Another way of describing the edge is that the edge 122 preferably has a shape that circumvents or avoids a portion of the plurality of electrode sites 150 when the substrate is rolled. The edge 122 is preferably on a lateral side of the substrate 120, preferably running approximately longitudinally in an axial direction along the carrier. As shown in FIGS. 8 and 11, the edge 122 may run axially along the entire length of the carrier. As shown in FIG. 9, in some embodiments the edge 122 may run axially along only a suitable portion of the entire carrier length, and may further include additional similar axial edges along other portions of the carrier length. In a first variation, as shown in FIG. 10, the edge 122 extends past and overlaps at least a portion of the rolled substrate 120, and preferably includes a set of extensions 124 that interleave with the outline of a portion of the electrode sites 150 on the rolled substrate, thereby circumventing the electrode sites to avoid obstruction. The set of extensions 124 preferably closely follow the edges of the electrode sites 150 and may, for example, be contoured in a curvilinear manner to include wavy extensions or shaped to include rectangular or square extensions, or any suitable extensions. The set of extensions may be regularly or irregularly spaced, and/or regularly or irregularly patterned. Alternatively, the edge 122 may be straight or curvilinear, without a set of extensions 124. In another example of the first variation, the substrate further includes a slot aligned axially along the carrier length, and the edge of the substrate extends past a portion of the substrate 120 and is inserted into the slot like a tab, thereby securing the "free" end of the rolled substrate that contains the edge. In this example, the edge may include features such as a wider tip that enhances the securement of the edge in the slot.

In a second variation, as shown in FIGS. 9 and 11, the substrate 120 may further include a second edge 123, opposite the first edge 122, that extends axially along the carrier and meets the first edge 122 in a complementary fashion when the substrate 120 is rolled. Similar to in the first variation, the first and/or second edge preferably includes a set of extensions that interleave with the outline of a portion of the electrode site, thereby circumventing the electrode sites 150 to avoid obstruction.

The plurality of conductive metal traces 140 in the electrode array function to transmit electrical signals, such as recording and/or stimulation signals to the plurality of electrode sites 150. To improve electrode array efficiency and functionality, the traces 140 preferably have equal and minimized impedance, to avoid irregularities of charge distribution and to reduce overall power consumption. Since each trace preferably terminates at an electrode site associated with that trace, there are more traces towards the proximal end of the electrode array than towards the distal end of the electrode array. Therefore, to achieve equal impedance among the traces 140, trace width preferably varies with respect to trace length, and more preferably, as shown in FIG. 11, the trace width is preferably increased for longer traces. For example, between a first conductive trace having a first distal end and a second conductive trace longer than the first conductive trace and having a second distal end, the second distal end is preferably wider than the first distal end. To minimize overall impedance, the traces are preferably arranged in the substrate 120 such that the traces cover as much substrate surface area as possible, while providing electrical isolation between adjacent traces.

The plurality of conductive traces 140 may be arranged on the substrate 120 in at least one of several variations of patterns. As shown in FIG. 8, in a first variation, the traces 140' are preferably arranged laterally along the substrate 120, continuing off a lateral side of the substrate 120 and utilizing nearly the entire length of the substrate, thereby retaining full coverage of the substrate 120 area. In this variation, lateral traces 140' are preferably shorter and wider due to having more available width, and therefore have lower impedance. As shown in FIG. 10, construction of a three-dimensional cylindrical electrode array with lateral traces 140' preferably includes wrapping the planar electrode array, such that the lateral trace ends that are "free" (not bonded to electrode sites) are wrapped within the electrode array and pre-formed into an arrangement of circumferential rings on the carrier. This is preferably completed by wrapping the planar electrode array, positioning the planar electrode array in a mold and then placing the mold and electrode array in a furnace to be tempered, but may alternatively be completed by any suitable process that alters the physical shape of the planar substrate. In this variation, as shown in FIG. 8, the traces 140' are preferably gathered in conductive interconnects 142 that transmit electrical signals toward the proximal end of the electrode array. The interconnects 142 preferably pass axially in the rolled substrate 120 and preferably continue axially within the carrier. As shown in FIG. 12E, the interconnects are preferably insulated within the carrier. The interconnects are preferably made of titanium and/or gold, but may additionally and/or alternatively include any suitable material. As shown in FIG. 11, in a second variation, the traces 140" preferably extend axially (e.g., extending longitudinally from proximal to distal) along the substrate 120, continuing off the proximal end of the substrate 120. In this variation, the traces 140" preferably are parallel to the axial edge 122 and follow the profile of axial edge 122, thereby retaining full coverage of the substrate area to lower overall impedance. Longitudinal traces 140" are preferably longer and therefore have slightly higher equalized impedance than the lateral traces of the first variation. The substrate 120 in the second trace pattern variation is preferably longer but narrower than the substrate 120 in the first trace pattern variation for the same finished three-dimensional electrode array shape. Construction of a three-dimensional electrode array with longitudinal traces 140" is preferably similar to that for an electrode array with lateral traces 140', except that the longitudinal traces 140 are preferably not wrapped within the electrode array. Although the traces 140 are preferably arranged in one of these variations of patterns, the traces 140 may alternatively be arranged in any suitable pattern for conducting electrical signals to the electrode sites 150. As shown in FIG. 12C, the plurality of conductive traces 140 are preferably patterned from the first layer of metal on the substrate 120, sandwiched between the first and second layers of insulating polymer, and are preferably made of polysilicon, although the conductive traces 140 may alternatively be made of any suitable conductive material.

The plurality of electrode sites 150 of the preferred embodiments functions to electrically communicate with the tissue, or any other suitable substance, that it has been implanted in or coupled to. The electrical communication is preferably a high-frequency, pulsed electric current; electrical stimulation in monopolar, bipolar, tripolar, and/or quadrapolar modes; a recording of electrical signals; data transmission; and/or any suitable electrical communication.

The electrode array of the three-dimensional variation may be coupled to the carrier. As shown in FIG. 1, the electrode sites 150 are preferably arranged both circumferentially around the carrier 170 and axially along the carrier 170 in a staggered, triangular lattice pattern 152. As best shown in FIGS. 8-11, the triangular lattice 152 is preferably an equilateral triangular (sometimes referred to as hexagonal) lattice, but may alternatively be an isosceles triangular (rhombic) lattice, or a scalene triangular (parallelogrammic) lattice. Alternatively, the electrode sites 150 may be arranged circumferentially around the carrier 170 and axially along the carrier 170 in a linear rectangular or square lattice pattern, or any suitable pattern. In some embodiments, the electrode sites 150 may be arranged in a combination of different lattices. For example, one portion of the electrode array may include a portion of electrode sites 150 arranged in a hexagonal lattice, while another portion of electrode sites 150 may be in a parallelogrammic lattice. The staggered, triangular lattice pattern 152 of electrode sites 150 may provide one or more of the following advantages. First, the staggered layout pattern is compact, optimizing use of the electrode array surface area for more electrode sites 150 for a given area, increasing resolution of stimulation control. Having a higher resolution of electrode site layout also increases reliability of the electrode array through fault tolerance, since if a particular electrode site becomes non-functional, other closely neighboring electrode sites 150 may be utilized with little difference in therapeutic effect. A second advantage is that the staggered layout pattern 152 includes electrode sites arranged in a higher number of different angular positions around the electrode array, allowing the electrode array to have more directionality than, for example, in a linear rectangular array of electrode sites, thereby enabling finer electrode stimulation control. As shown in FIG. 2, a third advantage is that the staggered layout pattern 152 allows electrode sites to have equidistant edge-to-edge spacing 154, which equalizes interaction between adjacent electrode sites 150, such that unintended effects due to unequal or asymmetrical electrode site interaction are reduced.

Figure 4A:
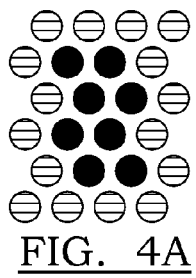
FIGS. 4A, 4B, and 4C are an unwrapped planar view, a perspective view, and a cross-sectional axial view, respectively, of an example activation pattern activating electrode sites partially circumferentially around the carrier.
Figure 5A:
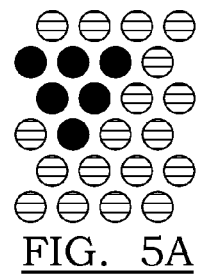
FIGS. 5A, 5B, and 5C are an unwrapped planar view, a perspective view, and a cross-sectional axial view, respectively, of an example activation pattern activating electrode sites axially along the carrier.
Figure 3B:
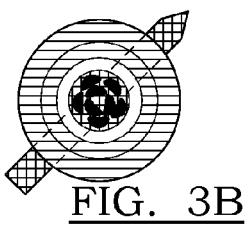
Figure 4B:
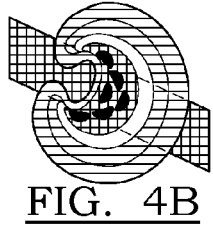
Figure 5B:
Figure 3C:
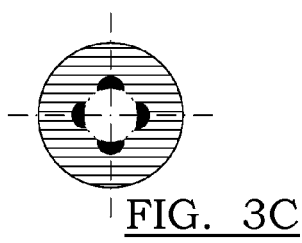
Figure 4C:
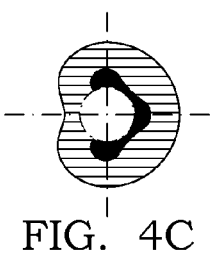
Figure 5C:
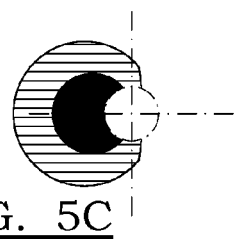
Figure 6A:
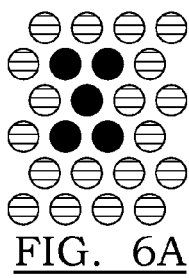
FIGS. 6A, 6B, and 6C are an unwrapped planar view, a perspective view, and a cross-sectional axial view, respectively, of a second example activation pattern activating electrode sites axially along the carrier.
Figure 7A:
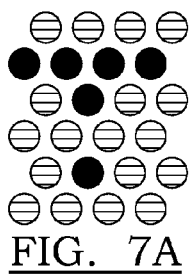
FIGS. 7A and 7B are an unwrapped planar view and a perspective view, respectively, of an example activation pattern activating electrode sites around and along the carrier.
Figure 6B:
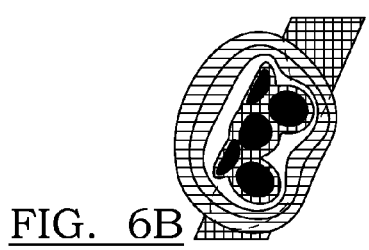
Figure 7B:
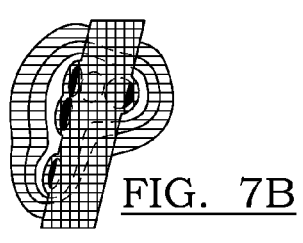
Figure 6C:
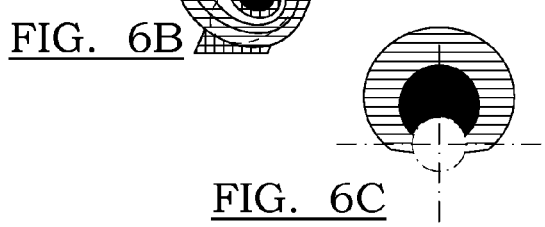

The plurality of electrode sites 150 can be activated individually or in selectable groups of electrode sites. The simultaneous activation of a group of electrode sites creates an activation pattern, generates an electric field in the tissue medium having a spatial distribution of current density, and influences the pattern of neural excitation. This will provide dynamic tunable electrical stimulation ranging from macroscale activation to more selective directional activation patterning using smaller subarrays or groups of sites along or around the carrier. Activation patterns of the electrode sites 150 of the electrode array may be translated in several different dimensions, as exemplified in FIGS. 3-7. The activation pattern from the electrode array may be translated circumferentially entirely around the carrier (shown in FIG. 3), which emulates a ring electrode for macroscale activation; circumferentially partially around the carrier (shown in FIG. 4); axially along the carrier (shown in FIGS. 5 and 6); any combination thereof (shown in FIG. 7); or any suitable or desired activation pattern. Additionally, each of the electrode sites 150 may be activated with an independent activation intensity. Each activation intensity may be individually distinct, or groups of electrode sites 150 may each have the same activation intensity. This form of multi-dimensional stimulation pattern programming, with tunable dimensions including spatial and activation intensity, provides a large tunable range of the neural interface system. The flexibility and precision provided by the plurality of electrode sites 150 also allows for adjustments by electrical means. Examples of adjustments include adapting to changes in the environment surrounding the electrode array, such as altered tissue conductivity due to tissue encapsulation or other reasons, and making slight corrections for a malpositioned electrode.

The excitation of tissue surrounding an electrode site is determined by factors including conductivity of the tissue, electrochemical properties of the individual electrode site and by geometric properties of the entire electrode array and carrier assembly. For an electrode array with several electrode sites activated simultaneously, the activation pattern, and therefore the current flow surrounding the electrode, is complex, resulting in an equally complex pattern of tissue excitation. At a basic level, the spreading resistance of an electrode site may determine the ability of the site to deliver charge to excitable tissue. When several electrode sites on an electrode array are activated simultaneously, there is an interaction of the electrode sites and activation patterns. For example, a first activation pattern may be modulated with the activation of a second distinct group of electrode sites, and multiple groups of activated electrode sites can be overlapping or non-overlapping.

The electrode sites 150 are preferably in the shape of ellipses, which may include circles and ellipses with an eccentricity between 0 and 1. However, the electrode sites may be any suitable shape. For eccentric elliptical electrode sites, the minor axis is preferably aligned axially along the carrier (electrode sites are "stretched" circumferentially), but the major axis may alternatively be aligned axially along the carrier (electrode sites are "stretched" axially). In other alternative embodiments, the lattice pattern of electrode sites 150 may be angled such that major and minor axes of the electrode sites 150 are neither circumferentially nor axially aligned. Equidistant spacing of electrode sites 150 may be achieved by having elliptical-shaped electrode sites and adjusting the lengths of the major and minor axes of the elliptical shapes in relation to the outer diameter of the carrier and/or desired electrode site spacing. Assuming a cylindrical carrier 170, equidistant spacing, identical electrode site shape and size, and orthogonal orientation of the electrode sites 150 relative to the carrier (axes of ellipses running axially and circumferentially), the relationship between the eccentricity E of elliptical electrode sites (in terms of "x" and "y", the axis lengths in the axial and circumferential directions, respectively), the outer diameter "D" of the carrier, and the electrode site spacing "a" may be summarized as $(y/x) \sim (D/a)$. In other words, the ratio of the circumferential ellipse axis to the axial ellipse axis is preferably proportional to the outer diameter of the carrier and inversely proportional to the electrode site spacing. Furthermore, the amplitude of the extensions 124 on the edge 122 of the substrate 120 (e.g., the degree to which the edge deviates from being a straight line) is preferably proportional to the ratio y/x, For example, for a given site spacing "a", the smaller the carrier diameter "D", the more eccentric the elliptical electrode sites must be, "stretched" in the axial direction, in order to have increased circumferential spacing to maintain the equidistant site spacing "a". As the electrode sites become more eccentric in the axial direction, the ratio of their axes "y/x" also decreases as the axial ellipse axis "x" becomes longer than the circumferential ellipse axis "y", and the amplitude of the extensions on the substrate edge decreases as it may more closely resemble a straight line to avoid obscuring any the plurality of electrode sites 150.

The electrode sites 150 are preferably identical in size and shape, in particular to maintain equidistant edge-to-edge spacing and to maximize positioning efficiency of a staggered layout pattern, but the plurality of electrode sites 150 may alternatively include electrode sites of different sizes and/or shape. The particular size of the electrode sites 150 preferably optimizes population of the electrode array surface area with the electrode sites, balancing the advantages and disadvantages of larger and smaller electrode sites. In particular, larger electrode sites may have the ability to deliver larger stimulation currents from individual electrode sites and/or groups of electrode sites, thereby allowing more options for current distribution and activation patterns, such as for a wider variety of stimulations and therapies. Larger electrode sites also may experience less electrochemical stress and lower charge densities than smaller electrode sites for a given amount of delivered current, by distributing the energy across a larger area. However, undesirable electrical interaction between electrode sites may be reduced when the electrode sites are smaller. Smaller electrode sites may also allow for more efficient population of a given surface area and provide finer stimulation control. The electrode sites are preferably patterned from the second metal layer 132 deposited on the substrate, and are preferably made of platinum, although the electrode sites 150 may alternatively be made of any suitable conductive material.

As shown in FIG. 1, one specific variation of the electrode array preferably includes sixty-four stimulation elliptical electrodes positioned circumferentially around and axially along the carrier, and more preferably the sixty-four stimulation electrodes are arranged in sixteen staggered rings of four stimulation electrodes, such that each electrode site is longitudinally aligned with one electrode site from each of seven other rings and laterally aligned with three other electrode sites in the same ring. The electrode array may alternatively and/or additionally include recording electrodes or any suitable kind of electrode. As shown in FIG. 2, the electrode sites are preferably positioned such that they have equidistant edge-to-edge spacing of approximately 0.20 millimeters. The electrode sites are preferably elliptical in shape, with a major axis length of preferably approximately 0.80 millimeters and a minor axis length of preferably approximately 0.666 millimeters.

2. The Carrier

As shown in FIG. 1, the carrier 170 of the preferred embodiments functions to support the electrode array. The carrier 170 may further function to shuttle the electrode array 110 into tissue or another suitable substance. The shape of the carrier 170 is preferably tubular with about a 1-mm diameter, but may alternatively be any suitable shape of any suitable diameter for the desired functions. The carrier 170 may include a sharpened end adapted to penetrate the tissue and aid in the insertion of the carrier and the electrode array 12 into the tissue. The carrier 170 may further extend the functionality of the system 100 providing fluidic channels through which therapeutic drugs, drugs to inhibit biologic response to the implant, or any other suitable fluid may be transmitted. This provides for the precise delivery of specific pharmaceutical compounds to localized regions of the body, such as the nervous system, and could facilitate, for example, intraoperative mapping procedures or long-term therapeutic implant devices. The fluidic channels may also provide a location through which a stiffener and/or stylet may be inserted to aid with implantation. Alternatively, the carrier may further include a separate lumen through which the stiffener or stylet may be inserted.

The carrier is preferably one of several variations. In a first variation, the carrier is a polymeric carrier. The carrier is preferably made of a polymer such as polyimide or silicone, but may be alternatively made from any other suitable material. The carrier may also include additional insulating polymers, such as parylene, that insulate conductive interconnects. The carrier is preferably flexible, but may alternatively be rigid or semi rigid. In a second variation, the carrier is a metal carrier. The carrier in this variation may be a solid metal tube or cylinder, or it may alternatively be perforated or not solid in any other suitable fashion. In a third variation, the carrier is a resorbable carrier, which is resorbed into tissue after a period of time, and upon resorption, the electrode array will be left to float freely in the brain or other suitable tissue or material. The resorbable carrier is preferably made of implantable medical fabric woven or knitted from a bioresorbable polymer. The bioresorbable polymer is preferably polyglycolide or polylactide, but may alternatively be made from any suitable bioresorbable material. Although the carrier is preferably one of these three variations, the carrier may alternatively be any suitable element to shuttle the electrode array and the connector into tissue or other substances and provide structural support.

3. Additional Components

The neural interface system may further include a guiding element that positions the series of electrode arrays in a three dimensional arrangement, or the electrode arrays may alternatively be arranged in a three dimensional manner without an additional guiding element. The guiding element is preferably similar to the guiding element described in U.S. patent application Ser. No. 11/932,903, filed on 31 Oct. 2007 and entitled "Neural Interface System", which is incorporated in its entirety by this reference.

The neural interface system may further include a second electrical subsystem that functions to operate with the electrode array. The second electrical subsystem is preferably at least one of several variations of suitable electronic subsystems to operate with the electrode array or any combination thereof. The second electrical subsystem may be a printed circuit board with or without onboard integrated circuits and/or on-chip circuitry for signal conditioning and/or stimulus generation, an Application Specific Integrated Circuit (ASIC), a multiplexer chip, a buffer amplifier, an electronics interface, an implantable pulse generator (that produces a high-frequency, pulsed electric current), an implantable rechargeable battery, integrated electronics for either real-time signal processing of the input (recorded) or output (stimulation) signals, integrated electronics for control of the fluidic components, any other suitable electrical subsystem, or any combination thereof.

The neural interface system may further include a connector that functions to couple the electrode array to the second electrical subsystem. The connector is preferably a ribbon cable, and more preferably a polymer ribbon cable, but may alternatively be any suitable kind of ribbon cable or other suitable element to couple the electrode array to the second electrical subsystem, such as wires or conductive interconnects.

The neural interface system may further include a stylet that functions to penetrate the tissue or other suitable substance and/or to provide structural support for the neural interface system during implantation. The stylet is preferably inserted into a lumen of the carrier, but may alternatively be located and/or inserted into any suitable component of the system in any suitable manner.

The neural interface system may further include a guide tube that functions to facilitate the insertion of the electrode array and/or to provide structural support for the neural interface system during implantation.

In addition to the above details, the second electrical subsystem, connector, stylet, and guide tube are preferably similar to those described in U.S. patent application Ser. No. 11/932,903, as referenced above, but may alternatively be of any suitable design, structure and/or build.

4. Method of Implanting a Neural Interface System

Figure 14A:
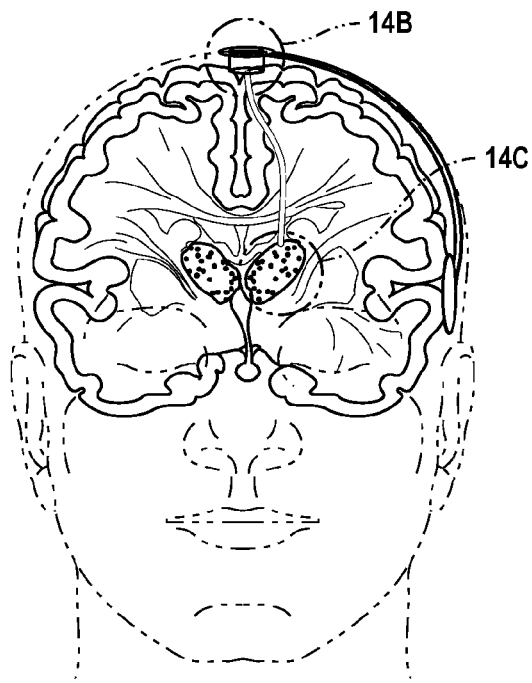
FIG. 14 is a schematic drawing of the neural interface system implanted in a patient.
Figure 14B:
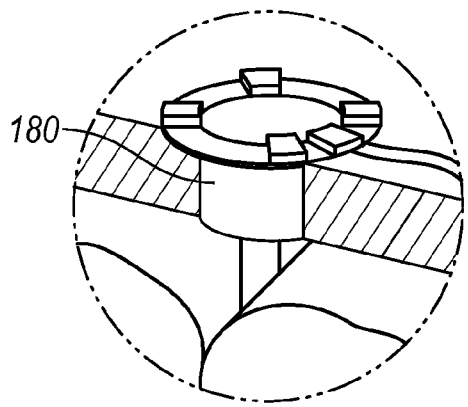
Figure 14C:
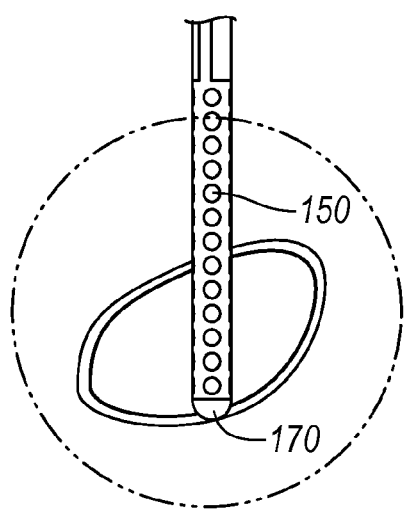

A method of implanting an neural interface system, as shown in FIG. 14, preferably comprises any combination of the following steps (or any other suitable steps):
  attaching a chamber 180 to the skull (preferably in a cranial burr-hole) of a patient;
  implanting, through the guide tube and/or with a stylet, an electrode array coupled via a connector to a second electrical subsystem;
  removing the guide tube over the second electrical subsystem and/or removing the stylet;
  placing the second electrical subsystem within the chamber 180; and
  sealing the electrical subsystems within the chamber 180.

Although omitted for conciseness, the preferred embodiments include every combination and permutation of the various electrode arrays, the various carriers, the various electrical subsystems and connectors, and the various guide tubes and stylets.

5. Method of Making a Neural Interface System

In general, the techniques for fabrication of the electrode array and the electrode sites are preferably similar to those used to create integrated circuits and therefore preferably use similar substrate, conductor, and insulating materials. Except as described below, the fabrication process and materials for the electrode array and electrode sites are preferably similar to those described in U.S. patent application Ser. No. 11/932,903, as referenced above, but may alternatively be any suitable process and/or be made of any suitable materials. As shown in FIGS. 10 and 13, the method of making a neural interface system 200 preferably includes the steps of providing a flexible substrate S210 having an edge shaped with a set of extensions; depositing a first polymer layer on the substrate S220; building on the first polymer layer a plurality of conductive traces that conduct electrical signals S230; depositing a second polymer layer on the substrate S240; building a plurality of electrode sites, coupled to the plurality of conductive traces, in a triangular lattice S250; and rolling the substrate towards the edge S260 to form a three-dimensional electrode array such that the plurality of electrode sites face externally and the set of extensions interleave with a portion of the plurality of electrode sites, thereby allowing the triangular lattice to be uninterrupted.

The step of providing a flexible substrate S210 having an edge with a set of extensions functions to provide a base material onto which subsequent layers are deposited and patterned to form an electrode array. Step 210 of providing a flexible substrate preferably includes providing a substrate and removing selected portions of the substrate to form the set of extensions. The set of extensions are preferably shaped as described above in Section 1. Removal of substrate material to form the set of extensions may be performed by cutting, grinding, sanding, polishing, and/or any suitable process. Alternatively, the set of extensions may be formed by molding the substrate, or any suitable process. The flexible substrate may include two or more edges with a set of extensions.

The step of depositing a first polymer layer on the substrate S220 functions to provide a lower layer of insulation for conductive materials including the conductive traces. The step of depositing a first polymer layer preferably includes depositing at least one layer of silicon dioxide and/or silicon nitride. As shown in FIGS. 12A to 12E, the first polymer layer preferably includes multiple layers of silicon dioxide, silicon nitride, and/or any suitable insulating polymer, and more preferably in an alternating manner. The layers are preferably approximately 10 micrometers thick, and deposited generally uniformly on the substrate.

Step 230, which includes building a plurality of conductive traces that conduct electrical signals on the first polymer layer, functions to form conductive interconnects that communicate with the plurality of electrode sites. The step of building a plurality of conductive traces preferably includes depositing a first layer of metal onto the first polymer layer and patterning the metal layer to form the plurality of conductive traces. The layer of metal preferably includes polysilicon, but may additionally and/or alternatively include any suitable material for conducting electrical signals. Patterning the metal layer may be one of or a combination of several variations. In a first variation, patterning the metal layer includes forming a plurality of lateral conductive traces arranged in a lateral direction generally orthogonal to the edge. In other words, in this variation, the lateral direction is preferably one such that a line drawn in the lateral direction divides a proximal portion and a distal portion of the electrode array. In a second variation, patterning the metal layer includes forming a plurality of longitudinal conductive traces arranged in a longitudinal direction generally parallel to the edge. In this variation, the longitudinal direction is preferably one such that a line drawn in the longitudinal direction may pass from a proximal portion to a distal portion of the electrode array. In a third variation, patterning the metal layer includes forming a plurality of angled conductive traces arranged in a non-orthogonal angle relative to a proximal end of the electrode array.

The step of depositing a second polymer layer on the substrate S240 is preferably similar to the step of depositing a first polymer layer on the substrate, except that portions of the second polymer layer preferably cover the plurality of conductive traces to contain the plurality of conductive traces between the first and second polymer layers for insulating purposes. In some embodiments, the method may further include the step of building a plurality of bond pads that couple the electrode sites to the conductive traces. The bond pads may be patterned from gold or any other suitable conductive material in a manner similar to the conductive traces and electrode sites.

Step 250, which includes building a plurality of electrode sites coupled to the plurality of conductive traces, functions to construct electrodes that provide neural stimulation and/or recording. The step of building preferably includes depositing a second metal layer on the substrate S252 and patterning the second metal layer to form a plurality of electrode sites S254. The electrode sites are preferably formed in a triangular lattice, and preferably have equidistant edge-to-edge spacing. As described in the neural interface system in Section 1, the triangular lattice is preferably an equilateral triangular (hexagonal) lattice, but may alternatively be an isosceles triangular (rhombic) lattice, or a scalene triangular (parallelogrammic) lattice. Alternatively, the electrode sites may be arranged arcuately around the carrier and axially along the carrier in a linear rectangular or square lattice pattern, or any suitable pattern. In some embodiments, the electrode sites may be arranged in a combination of different lattices. For example, one portion of the electrode array may include a portion of electrode sites arranged in a hexagonal lattice, while another portion of electrode sites may be in a parallelogrammic lattice.

The method preferably further includes the step of building an external polymer layer S270, which preferably includes depositing a third polymer layer on the substrate and patterning the third polymer layer to expose the electrode sites. The polymer layer is preferably an insulating polymer such as parylene, but may alternatively be any suitable material.

Step 260 (FIG. 10), which includes rolling the substrate towards the edge to form a three-dimensional electrode array, functions to form a three-dimensional electrode array. The step of rolling the substrate preferably enables the plurality of electrode sites to be arranged facing externally. The step of rolling the substrate allows the set of extensions on the edge of the substrate to interleave with a portion of the plurality of electrode sites, thereby allowing the triangular lattice to be uninterrupted circumferentially around and axially along the electrode array. The electrode array is preferably cylindrical, but may have any suitable cross-sectional shape, such as an eccentric ellipse, a v-shape, or crescent cross section. In a first variation, in which the conductive traces are arranged in a lateral direction, the step of rolling the substrate preferably includes wrapping the lateral conductive traces arcuately within the rolled substrate such that the lateral conductive traces are arranged in circumferential rings. In rolling the substrate towards the lateral edge, the lateral edge is the "free" end overlapping a portion of the substrate. In a second variation, in which the conductive traces are arranged in a longitudinal direction, the step of rolling the substrate preferably includes allowing the longitudinal conductive traces to pass axially along the three-dimensional array, running from a proximal end to a distal end of the electrode array. The method preferably further includes placing the rolled substrate in a mold and tempering the rolled substrate, such as in furnace.

The method preferably includes coupling a carrier to the electrode array to support the electrode array, which functions to assemble components of the neural interface system. Coupling a carrier to the electrode array may include any of the following steps, any suitable additional steps, and any combination of steps thereof: connecting the electrode array to the connector, connecting a second electrical subsystem to the connector, pre-forming the electrode array, connecting a set of interconnects, and injection molding a silicone element.

As a person skilled in the art will recognize from the previous detailed description and from the figures and claims, modifications and changes can be made to the preferred embodiments of the invention without departing from the scope of this invention defined in the following claims.

We claim:

1. A neural interface system, comprising:
 a) a substrate that is configured to be formed into a three-dimensional shape and comprises spaced apart first and second lateral edges extending from a proximal edge to a distal edge, wherein the first and second lateral edges comprise respective first and second wavy shapes curving alternatively in opposite lateral directions as they extend axially at least part way from the proximal edge to the distal edge of the substrate;
 a plurality of conductive traces patterned on the substrate and adapted to transmit electrical signals; and
 c) a plurality of electrode sites supported on the substrate and individually electrically coupled to one of the plurality of conductive traces; and
 e) a carrier supporting the substrate in a three-dimensional shape, wherein the first wavy shape of the first lateral edge is interleaved with the second wavy shape of the second lateral edge to thereby form an interleaved boundary at the first and second lateral edges of the substrate supporting the electrical sites and the conductive traces on the carrier.

2. The neural interface system of claim 1, wherein the second lateral edge overlaps a portion of the substrate at the first lateral edge.

3. The neural interface system of claim 1, wherein the plurality of conductive traces are arranged in circumferential rings around the carrier.

4. The neural interface system of claim 3, wherein the plurality of conductive traces includes a first conductive trace having a first distal end and a second conductive trace having a second distal end, wherein the second conductive trace is longer than the first conductive trace and the second distal end has a wider cross-section perpendicular to an axial extent of the second conductive trace than the first distal end.

5. The neural interface system of claim 1, wherein the plurality of conductive traces extend axially along the carrier.

6. The neural interface system of claim 5, wherein the plurality of conductive traces are parallel to at least one of the first and second lateral edges of the substrate.

7. The neural interface system of claim 5, wherein the plurality of conductive traces includes a first conductive trace having a first distal end and a second conductive trace having a second distal end, wherein the second conductive trace is longer than the first conductive trace and the second distal end has a wider cross-section perpendicular to an axial extent of the second conductive trace than the first distal end.

8. The neural interface system of claim 1, wherein at least one of the plurality of electrode sites is eccentric and has a minor axis and a major axis that is longer than the minor axis.

9. The neural interface system of claim 8, wherein the minor axis is aligned axially along the carrier.

10. The neural interface system of claim 1 wherein the carrier has a substantially circular cross-section perpendicular to a longitudinal axis of the carrier.

11. The neural interface system of claim 10 wherein the plurality of electrode sites are arranged in a triangular lattice circumferentially around and axially along the carrier.

12. The neural interface system of claim 11, wherein the triangular lattice is an equilateral triangular lattice.

13. The neural interface system of claim 11, wherein the plurality of electrode site are distributed in the triangular lattice with equal edge-to-edge spacing.

14. The neural interface system of claim 13, wherein a ratio of the major axis to the minor axis of the plurality of the electrode sites is:
   a) proportional to an amplitude of the first and second wavy shapes comprising the respective first and second lateral edges;
   b) proportional to an outer diameter of at least one of the electrode sites; and
   c) inversely proportional to the edge-to-edge spacing.

15. The neural interface system of claim 1 wherein the interleaved boundary extends axially along the carrier between a right axial row portion of the plurality of electrode sites adjacent to the first lateral edge and a left axial row portion of the plurality of electrode sites adjacent to the second lateral edge of the substrate.

16. The electrode array of claim 1 wherein the plurality of electrode sites includes at least one of a recording electrode site and a stimulation electrode site.

17. The electrode array of claim 1 wherein the plurality of electrode sites are arranged in a triangular lattice circumferentially around and axially along the carrier.

18. The electrode array of claim 1 wherein the electrode sites have either a circular or elliptical shape with an eccentricity ranging from 0 to 1.

19. A method of making a neural interface system, comprising the steps of:
   a) providing a flexible substrate comprising spaced apart first and second lateral edges extending from a proximal edge to a distal edge, wherein the first and second lateral edges comprise respective first and second wavy shapes curving alternatively in opposite lateral directions as they extend axially at least part way from the proximal edge to the distal edge of the substrate;
   b) depositing a first polymer layer on the substrate;
   c) building a plurality of conductive traces on the first polymer layer;
   d) depositing a second polymer layer on the substrate;
   e) building a plurality of electrode sites that are individually electrically coupled to one of the plurality of conductive traces; and
   f) forming a carrier supporting the substrate including the electrode array into a three-dimensional electrode array such that the first wavy shape of the first lateral edge is interleaved with the second wavy shape of the second lateral edge to thereby form an interleaved boundary at the first and second lateral edges.

20. The method of claim 19, including removing selected portions of the substrate to form the first and second lateral edges comprising the respective first and second wavy shapes.

21. The method of claim 19, wherein the step of building a plurality of conductive traces includes depositing a metal layer on the first polymer layer and patterning the metal layer to form the plurality of conductive traces.

22. The method of claim 21, wherein the step of patterning the metal layer to form the plurality of conductive traces includes forming a plurality of lateral conductive traces arranged in a lateral direction generally orthogonal to at least one of the first and second lateral edges.

23. The method of claim 21, wherein the step of patterning the metal layer to form the plurality of conductive traces includes forming a plurality of longitudinal conductive traces arranged in an axial direction generally parallel to at least one of the first and second lateral edges.

24. A neural interface system, which comprises:
   a) an electrode array comprising:
      i) a substrate provide in a three-dimensional shape;
      ii) a plurality of conductive traces patterned on the substrate; and
      iii) a plurality of elliptically shaped electrode sites coupled to the plurality of conductive traces, wherein the electrode sites include at least one of a recording electrode site and a stimulation electrode site that is configured to electrically communicate with its surroundings; and
   b) a carrier that supports the electrode array;
   c) wherein the plurality of electrode sites are arranged in a triangular lattice circumferentially around and axially along the carrier; and
   d) wherein the substrate includes a longitudinal edge that extends axially along the carrier and is constrained between a first axial row portion of the plurality of electrode sites and a second axial row portion of the plurality of electrode sites adjacent to the first axial row portion;
   e) wherein the longitudinal edge of the substrate includes a set of undulatory extensions with a ratio of a major axis of the plurality of electrode sites to a minor axis of the plurality of the electrode sites being:

i) proportional to the amplitude of the set of undulations;
ii) proportional to an outer diameter of the three-dimensional shape of the substrate; and
iii) inversely proportional to the edge-to-edge spacing.

25. The neural interface system of claim 24 wherein the triangular lattice is an equilateral triangular lattice.

26. The neural interface system of claim 24 wherein the plurality of electrode sites are distributed in the triangular lattice with equal edge-to-edge spacing.

27. A method of making a neural interface system, comprising the steps of:
 a) providing a flexible substrate comprises spaced apart first and second lateral edges extending from a proximal edge to a distal edge;
 b) removing selected portions of the substrate to form first and second lateral edges having respective first and second wavy shapes curving alternatively in opposite lateral directions as they extend axially at least part way from the proximal edge to the distal edge of the substrate;
 c) depositing a first polymer layer on the substrate;
 d) depositing a metal layer on the first polymer layer and patterning the metal layer to form a plurality of conductive traces;
 e) building a plurality of electrode sites coupled to the plurality of conductive traces;
 f) depositing a second polymer layer on the substrate; and
 g) rolling the substrate to interleave the first wavy shape of the first lateral edge with the second wavy shape of the second lateral edge to thereby form an interleaved boundary at the first and second lateral edges of the substrate supporting the electrical sites and the conductive traces on the carrier.

28. The method of claim 27 including arranging the electrode sites in a triangular lattice on the substrate.

29. The method of claim 28 including interleaving the extensions with a portion of the plurality of electrode sites, thereby providing the triangular lattice being uninterrupted.

30. An electrode array, which comprises:
 a) a substrate that is configured to be formed into a three-dimensional shape and comprises spaced apart first and second lateral edges extending from a proximal edge to a distal edge, wherein the first and second lateral edges comprise respective first and second wavy shapes curving alternatively in opposite lateral directions as they extend axially at least part way from the proximal edge to the distal edge of the substrate;
 b) a plurality of conductive traces patterned on the substrate; and
 c) a plurality of electrode sites supported on the substrate and individually electrically coupled to one of the plurality of conductive traces,
 d) wherein the first wavy shape of the first lateral edge is configured to interleave with the second wavy shape of the second lateral edge.

31. The electrode array of claim 30 wherein the plurality of electrode sites includes at least one of a recording electrode site and a stimulation electrode site.

32. The electrode array of claim 30 wherein the plurality of electrode sites are arranged in a triangular lattice circumferentially around and axially along the carrier.

33. The electrode array of claim 30 wherein the electrode sites have either a circular or elliptical shape with an eccentricity ranging from 0 to 1.

34. An electrode array, which comprises:
 a) a substrate that is configured to be formed into a three-dimensional shape and comprises spaced apart first and second lateral edges extending from a proximal edge to a distal edge, wherein the first and second lateral edges comprise respective first and second patterned shapes selected from the group consisting of wavy extensions, rectangular extensions and square extensions as the lateral edges extend axially at least part way from the proximal edge to the distal edge of the substrate;
 b) a plurality of conductive traces patterned on the substrate and adapted to transmit electrical signals; and
 c) a plurality of electrode sites supported on the substrate and individually electrically coupled to one of the plurality of conductive traces,
 d) wherein the first lateral edge is configured to interleave with the second lateral edge to thereby form an interleaved boundary at the first and second lateral edges.

35. The electrode array of claim 34 wherein the first and second patterned shapes are either regularly or irregularly spaced along the respective first and second lateral edges.

36. The electrode array of claim 34 wherein the first and second patterned shapes are either regularly or irregularly patterned along the respective first and second lateral edges.

* * * * *

UNITED STATES PATENT AND TRADEMARK OFFICE
CERTIFICATE OF CORRECTION

PATENT NO. : 8,332,046 B2
APPLICATION NO. : 12/848828
DATED : December 11, 2012
INVENTOR(S) : Anderson et al.

It is certified that error appears in the above-identified patent and that said Letters Patent is hereby corrected as shown below:

In the Claims:

Column 12, line 56 insert a --b)-- before the words "a plurality"

Column 13, line 42 replace the word "site" with "sites"

Signed and Sealed this
Twenty-eighth Day of May, 2013

Teresa Stanek Rea
*Acting Director of the United States Patent and Trademark Office*